(12) United States Patent
Long

(10) Patent No.: US 7,892,166 B2
(45) Date of Patent: Feb. 22, 2011

(54) MEDICAL INSTRUMENT INCLUDING A CATHETER HAVING A CATHETER STIFFENER AND METHOD FOR USING

(75) Inventor: Gary L. Long, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 576 days.

(21) Appl. No.: 11/436,397

(22) Filed: May 18, 2006

(65) Prior Publication Data

US 2007/0270649 A1   Nov. 22, 2007

(51) Int. Cl.
*A61B 1/00* (2006.01)
(52) U.S. Cl. .................. 600/144; 600/145; 600/149
(58) Field of Classification Search ............. 600/144, 600/145, 424, 143, 146, 148–151
See application file for complete search history.

(56) References Cited

U.S. PATENT DOCUMENTS

| | | | |
|---|---|---|---|
| 2,976,865 A * | 3/1961 | Shipley .................. 600/488 |
| 3,470,876 A | 10/1969 | Barchilon | |
| 3,521,620 A | 7/1970 | Cook | |
| 3,791,387 A | 2/1974 | Itoh | |
| 3,799,151 A | 3/1974 | Fakaumi et al. | |
| 3,805,791 A | 4/1974 | Seuberth et al. | |
| 4,102,478 A | 7/1978 | Samoilov | |
| 4,326,530 A | 4/1982 | Fleury, Jr. | |
| 4,493,320 A | 1/1985 | Treat | |
| 4,619,247 A | 10/1986 | Inoue et al. | |
| 4,638,802 A | 1/1987 | Okada | |
| 4,735,194 A | 4/1988 | Stiegmann | |
| 4,739,768 A | 4/1988 | Engelson | |
| 4,758,750 A | 7/1988 | Itagaki et al. | |
| 4,791,963 A | 12/1988 | Gronert et al. | |
| 4,884,557 A * | 12/1989 | Takehana et al. ............. 600/145 |
| 4,890,602 A * | 1/1990 | Hake .......................... 600/144 |
| 4,893,613 A | 1/1990 | Hake | |

(Continued)

FOREIGN PATENT DOCUMENTS

DE     4408730     9/1995

(Continued)

OTHER PUBLICATIONS

Ginsberg, G.G., "Colonoscopy with the variable stiffness colonoscope," Gastrointestinal Endoscopy, vol. 58, No. 4 (2003).

(Continued)

*Primary Examiner*—Linda C Dvorak
*Assistant Examiner*—Alireza Nia
(74) *Attorney, Agent, or Firm*—Victor C. Moreno

(57) ABSTRACT

A medical instrument including a medical catheter having a distal end insertable within a body lumen of a patient, having a first flexible catheter segment, and having a second flexible catheter segment located distal the first flexible catheter segment. The first flexible catheter segment includes a first loop sensor and includes an active first catheter stiffener adapted to stiffen and un-stiffen substantially only the first flexible catheter segment. The second flexible catheter segment includes a second loop sensor and includes an active second catheter stiffener adapted to stiffen and un-stiffen substantially only the second flexible catheter segment. A method for using the medical instrument is also presented.

13 Claims, 7 Drawing Sheets

U.S. PATENT DOCUMENTS

| | | | |
|---|---|---|---|
| 4,930,494 A * | 6/1990 | Takehana et al. | 600/145 |
| 4,963,147 A | 10/1990 | Agee et al. | |
| 5,002,041 A | 3/1991 | Chikama | |
| 5,035,696 A | 7/1991 | Rydell | |
| 5,066,295 A | 11/1991 | Kozak et al. | |
| 5,078,716 A | 1/1992 | Doll | |
| 5,171,314 A | 12/1992 | Dulebohn | |
| 5,201,732 A | 4/1993 | Parins et al. | |
| 5,201,741 A | 4/1993 | Dulebohn | |
| 5,250,060 A | 10/1993 | Carbo et al. | |
| 5,293,869 A | 3/1994 | Edwards et al. | |
| 5,322,505 A | 6/1994 | Krause et al. | |
| 5,342,299 A | 8/1994 | Snoke et al. | |
| 5,346,504 A | 9/1994 | Ortiz et al. | |
| 5,351,692 A | 10/1994 | Dow et al. | |
| 5,353,807 A | 10/1994 | DeMarco | |
| 5,397,304 A | 3/1995 | Truckai | |
| 5,409,453 A | 4/1995 | Lundquist et al. | |
| 5,431,671 A | 7/1995 | Nallakrishnan | |
| 5,433,721 A | 7/1995 | Hooven et al. | |
| 5,441,499 A | 8/1995 | Fritzch | |
| 5,482,029 A * | 1/1996 | Sekiguchi et al. | 600/109 |
| 5,522,829 A | 6/1996 | Michalos | |
| 5,531,664 A * | 7/1996 | Adachi et al. | 600/149 |
| 5,531,686 A | 7/1996 | Lundquist et al. | |
| 5,542,948 A | 8/1996 | Weaver et al. | |
| 5,618,294 A | 4/1997 | Aust et al. | |
| 5,628,719 A | 5/1997 | Hastings et al. | |
| 5,706,827 A | 1/1998 | Ehr et al. | |
| 5,728,044 A * | 3/1998 | Shan | 600/145 |
| 5,749,828 A | 5/1998 | Solomon et al. | |
| 5,752,961 A | 5/1998 | Hill | |
| 5,776,080 A | 7/1998 | Thome et al. | |
| 5,792,165 A | 8/1998 | Kileman et al. | |
| 5,810,715 A | 9/1998 | Moriyama | |
| 5,810,807 A | 9/1998 | Ganz et al. | |
| 5,836,947 A | 11/1998 | Fleischman | |
| 5,848,986 A | 12/1998 | Lundquist et al. | |
| 5,865,724 A | 2/1999 | Palmer et al. | |
| 5,897,554 A | 4/1999 | Chia et al. | |
| 5,972,012 A | 10/1999 | Ream et al. | |
| 6,066,102 A | 5/2000 | Townsend et al. | |
| 6,071,277 A | 6/2000 | Farley et al. | |
| 6,074,408 A | 6/2000 | Freeman | |
| 6,093,185 A | 7/2000 | Ellis et al. | |
| 6,093,195 A | 7/2000 | Ouchi | |
| 6,152,918 A | 11/2000 | Padilla et al. | |
| 6,174,280 B1 | 1/2001 | Oneda et al. | |
| 6,203,494 B1 * | 3/2001 | Moriyama | 600/144 |
| 6,352,503 B1 | 3/2002 | Matsui et al. | |
| 6,371,907 B1 | 4/2002 | Hasegawa et al. | |
| 6,395,001 B1 | 5/2002 | Ellman et al. | |
| 6,423,059 B1 | 7/2002 | Hanson et al. | |
| 6,443,943 B1 | 9/2002 | Ouchi | |
| 6,443,944 B1 | 9/2002 | Doshi et al. | |
| 6,450,948 B1 | 9/2002 | Matsuura et al. | |
| 6,451,014 B1 | 9/2002 | Wakikaido et al. | |
| 6,454,703 B1 | 9/2002 | Ide | |
| 6,454,758 B1 | 9/2002 | Thompson | |
| 6,475,222 B1 | 11/2002 | Berg et al. | |
| 6,482,149 B1 | 11/2002 | Torii | |
| 6,488,658 B1 | 12/2002 | Long | |
| 6,500,189 B1 | 12/2002 | Lang et al. | |
| 6,569,105 B1 | 5/2003 | Kortenbach et al. | |
| 6,579,300 B2 | 6/2003 | Griego et al. | |
| 6,602,267 B2 | 8/2003 | Castaneda | |
| 6,612,992 B1 * | 9/2003 | Hossack et al. | 600/467 |
| 6,663,616 B1 | 12/2003 | Roth et al. | |
| 6,663,625 B1 | 12/2003 | Ormsby et al. | |
| 6,709,388 B1 | 3/2004 | Mosse et al. | |
| 6,730,097 B2 | 5/2004 | Dennis | |
| 6,743,240 B2 | 6/2004 | Smith et al. | |
| 6,764,441 B2 | 7/2004 | Chiel et al. | |
| 6,866,626 B2 | 3/2005 | Long et al. | |
| 7,060,024 B2 | 6/2006 | Long et al. | |
| 7,060,025 B2 | 6/2006 | Long et al. | |
| 7,066,879 B2 | 6/2006 | Fowler et al. | |
| 7,093,518 B2 | 8/2006 | Gmeilbauer | |
| 7,118,587 B2 | 10/2006 | Dycus et al. | |
| 2001/0029397 A1 | 10/2001 | Thompson | |
| 2001/0037084 A1 | 11/2001 | Nardeo | |
| 2002/0017515 A1 | 2/2002 | Obata et al. | |
| 2002/0087208 A1 | 7/2002 | Koblish et al. | |
| 2002/0095168 A1 | 7/2002 | Griego et al. | |
| 2002/0120178 A1 | 8/2002 | Tartaglia et al. | |
| 2002/0147445 A1 | 10/2002 | Farley et al. | |
| 2002/0177802 A1 | 11/2002 | Moutafis et al. | |
| 2003/0014051 A1 | 1/2003 | Woloszko | |
| 2003/0045778 A1 | 3/2003 | Ohline et al. | |
| 2003/0074014 A1 | 4/2003 | Castaneda | |
| 2003/0109898 A1 | 6/2003 | Schwarz et al. | |
| 2003/0125788 A1 | 7/2003 | Long | |
| 2003/0153866 A1 | 8/2003 | Long et al. | |
| 2003/0181785 A1 | 9/2003 | Viebach et al. | |
| 2003/0195492 A1 | 10/2003 | Gobron et al. | |
| 2003/0208219 A1 | 11/2003 | Aznoian et al. | |
| 2004/0034343 A1 | 2/2004 | Gillespie et al. | |
| 2004/0044350 A1 | 3/2004 | Martin et al. | |
| 2004/0068291 A1 | 4/2004 | Suzuki | |
| 2004/0092953 A1 | 5/2004 | Salameh et al. | |
| 2004/0097919 A1 | 5/2004 | Wellman et al. | |
| 2004/0143159 A1 | 7/2004 | Wendlandt | |
| 2004/0143160 A1 | 7/2004 | Couvillon, Jr. | |
| 2004/0193016 A1 | 9/2004 | Root et al. | |
| 2004/0204645 A1 * | 10/2004 | Saadat et al. | 600/424 |
| 2004/0230096 A1 | 11/2004 | Stefanchik et al. | |
| 2005/0043743 A1 | 2/2005 | Dennis | |
| 2005/0183733 A1 | 8/2005 | Kawano et al. | |
| 2005/0203610 A1 | 9/2005 | Tzeng | |
| 2005/0222587 A1 | 10/2005 | Jinno et al. | |
| 2005/0234296 A1 | 10/2005 | Saadat et al. | |
| 2005/0272975 A1 | 12/2005 | McWeeney et al. | |
| 2005/0273084 A1 | 12/2005 | Hinmen et al. | |
| 2005/0273085 A1 | 12/2005 | Hinman et al. | |
| 2006/0009711 A1 | 1/2006 | Gingrich et al. | |
| 2006/0089627 A1 | 4/2006 | Burnett et al. | |
| 2007/0225562 A1 | 9/2007 | Spivey et al. | |

FOREIGN PATENT DOCUMENTS

| | | |
|---|---|---|
| DE | 19729499 | 1/1999 |
| EP | 0027704 | 4/1981 |
| EP | 0397489 | 11/1990 |
| EP | 1310206 | 5/2003 |
| EP | 2004-154164 | 6/2004 |
| EP | 1849421 | 10/2007 |
| JP | 59-181124 | 10/1984 |
| WO | WO 96/00030 | 1/1996 |
| WO | WO 97/12557 | 4/1997 |
| WO | 97/35135 | 9/1997 |
| WO | 99/12489 | 3/1999 |
| WO | 01/08737 | 2/2001 |
| WO | 01/82814 | 11/2001 |
| WO | 01/93938 | 12/2001 |
| WO | 02/43797 | 6/2002 |
| WO | 03/053225 | 7/2003 |
| WO | 03/092476 | 11/2003 |
| WO | 2005/113051 | 12/2005 |
| WO | 2006/019291 | 2/2006 |
| WO | 2006/026687 | 3/2006 |

| WO | 2006/122279 | 11/2006 |

OTHER PUBLICATIONS

Brooker, J.C. et al., "A new variable stiffness colonoscope makes colonoscopy easier: a randomised controlled trial," Gut 2000, 46, pp. 801-805 (2000).

Rex, D.K., "Effect of Variable Stiffness Colonoscopes on Cecal Intubation Times for Routine Colonoscopy by an Experienced Examiner in Sedated Patients," Endoscopy; 33 (1), pp. 60-64 (2001).

Shah, S.G., et al., "Magnetic imaging of colonoscopy: an audit of looping, accuracy and ancillary maneuvers," Gastrointestinal Endoscopy, vol. 52, No. 1, pp. 1-8 (2000).

Shah, S.G., et al., "The variable stiffness colonoscope: assessment of efficacy by magnetic endoscope imaging," Gastrointestinal Endoscopy, vol. 56, No. 2, pp. 195-201 (2002).

"Sensors-Resistance," Smart Engineering Group (1999).

Examination Report, European Application No. 07251728.7 (Dec. 17, 2008).

European Search Report, European Application No. 07251934 (2 pages) (dated Aug. 30, 2007).

* cited by examiner

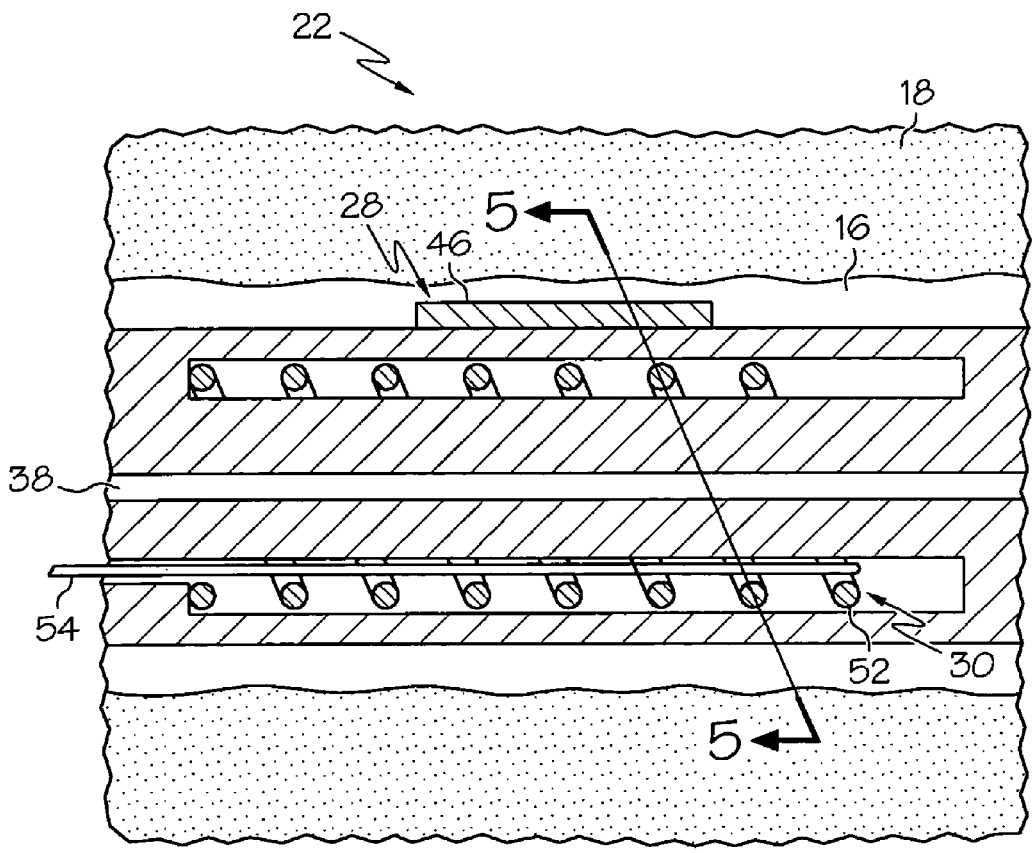
FIG. 4
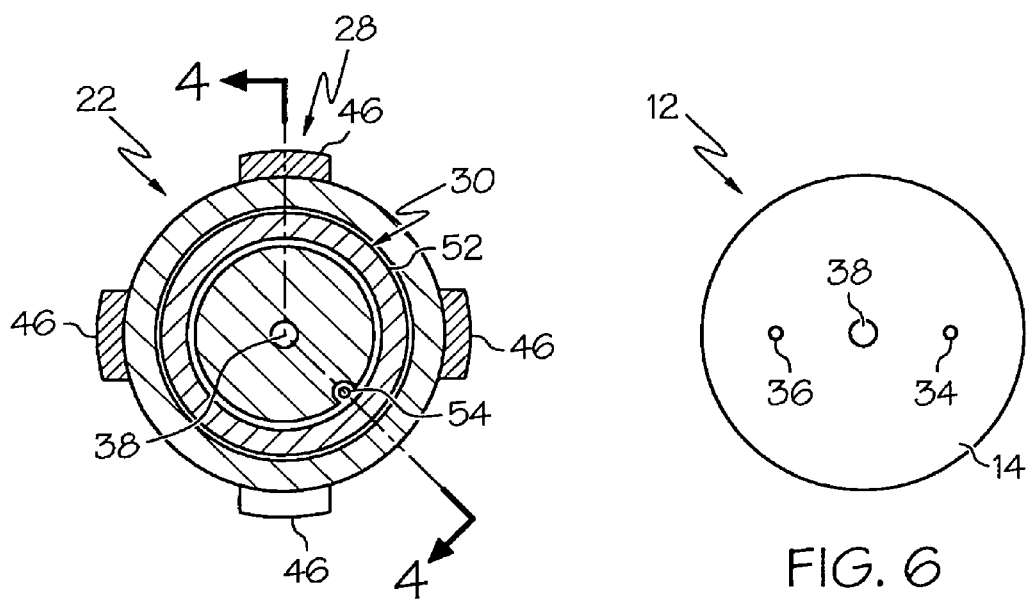
FIG. 5
FIG. 6

MEDICAL INSTRUMENT INCLUDING A CATHETER HAVING A CATHETER STIFFENER AND METHOD FOR USING

FIELD OF THE INVENTION

The present invention is related generally to medical equipment, and more particularly to a medical instrument including a catheter having a catheter stiffener and to a method for using the medical instrument.

BACKGROUND OF THE INVENTION

Examples of known catheters include, without limitation, flexible insertion tubes of endoscopes (including flexible insertion tubes of colonoscopes and enteroscopes). The insertion tube has an articulatable distal end portion controlled by wires running from the distal end portion to control knobs on the handle of the endoscope. A wide angle video camera in the distal end of the insertion tube permits medical observation. In use, the distal end of the insertion tube is inserted into a body lumen of a patient. The user manually pushes on a proximal tube portion to advance the distal end of the insertion tube within the body lumen for medical observation and/or medical treatment. In a serpentine body lumen, such as the colon, the articulatable distal end of the insertion tube can become misaligned in the body lumen and become blocked by lumen tissue from further advancement. Then, if the user further pushes on the proximal tube portion, the insertion tube forms undesirable loops which the user must correct before realigning the distal end of the insertion tube and further advancing the insertion tube within the body lumen.

A colonoscope is known which includes a flexible insertion tube having a helical coil running substantially ¾ of the distance from the proximal tube end toward the distal tube end. A pull cable is attached to the helical coil at the coil's distal end. Pulling on the pull cable by turning a stiffening knob on a handpiece stiffens the insertion tube along ¾ of its length, wherein the proximal end of the tube is attached to the handpiece and the proximal end of the pull cable is operatively connected to the stiffening knob. A user pulls on the pull cable when the distal end of the medical catheter is no longer moving, despite being manually pushed, as determined from the visualization device. The user resumes manually pushing the medical catheter with the now ¾-length-stiffened insertion tube.

Still, scientists and engineers continue to seek improved medical instruments including a catheter having a catheter stiffener and improved methods for using such medical instruments.

SUMMARY OF THE INVENTION

A first expression of a first embodiment of the invention is for a medical instrument including a medical catheter having a distal end insertable within a body lumen of a patient, having a first flexible catheter segment, and having a second flexible catheter segment located distal the first flexible catheter segment. The first flexible catheter segment includes a first loop sensor and includes an active first catheter stiffener adapted to stiffen and un-stiffen substantially only the first flexible catheter segment. The second flexible catheter segment includes a second loop sensor and includes an active second catheter stiffener adapted to stiffen and un-stiffen substantially only the second flexible catheter segment.

A first expression of a second embodiment of the invention is for a medical instrument including a medical catheter, wherein the medical catheter is a sheath and is adapted for installation over a flexible endoscope insertion tube having a distal-tube-end visualization device. The installed medical catheter has a distal end insertable within a body lumen of a patient, has a first flexible catheter segment, and has a second flexible catheter segment located distal the first flexible catheter segment. The first flexible catheter segment includes a first loop sensor and includes an active first catheter stiffener adapted to stiffen and un-stiffen substantially only the first flexible catheter segment. The second flexible catheter segment includes a second loop sensor and includes an active second catheter stiffener adapted to stiffen and un-stiffen substantially only the second flexible catheter segment.

A method of the invention is for using a medical instrument. The medical instrument includes a medical catheter. The medical catheter has a distal end insertable within a body lumen of a patient, has a first flexible catheter segment, and has a second flexible catheter segment located distal the first flexible catheter segment. The first flexible catheter segment includes a first loop sensor and includes an active first catheter stiffener adapted to stiffen and un-stiffen substantially only the first flexible catheter segment. The second flexible catheter segment includes a second loop sensor and includes an active second catheter stiffener adapted to stiffen and un-stiffen substantially only the second flexible catheter segment. The method includes inserting the distal end within the body lumen. The method also includes manually pushing the medical catheter to advance the medical catheter within the body lumen. The method also includes stopping manually pushing the medical catheter upon determining from a visualization device associated with the medical catheter that the distal end is no longer moving. The method also includes determining that undesirable looping is developing in the first flexible catheter segment 20 based at least on an output from the first loop sensor 24. The method also includes determining that undesirable looping is not developing in the second flexible catheter segment 22 based at least on an output from the second loop sensor 28. The method also includes using the first catheter stiffener to stiffen the first flexible catheter segment. The method also includes not using the second catheter stiffener to stiffen the second flexible catheter segment. The method also includes resuming manually pushing the medical catheter after using the first catheter stiffener to stiffen the first flexible catheter segment and not using the second catheter stiffener to stiffen the second flexible catheter segment.

Several benefits and advantages are obtained from one or more of the expressions of embodiments and the method of the invention. In a first example, having a multi-segment medical catheter with each segment having its own loop sensor and its own catheter stiffener to stiffen substantially only such segment allows a user more control in manually advancing the catheter within a body lumen of a patient. In one variation, a user stiffens only that segment or only those segments which are developing an undesirable loop as determined from the outputs of the loop sensors wherein such stiffening helps prevent further loop formation only in segments where needed while allowing flexibility in segments not developing an undesirable loop. In the same or a different variation, a user takes into account the location of the segments in the body lumen in deciding which segments should be stiffened.

In one utilization wherein the catheter is a flexible insertion tube of a colonoscope, when the distal tip of the insertion tube is being advanced through the sigmoid, the operator will articulate the distal end. In this example, when the distal tip is advanced into the descending colon, a segment just behind the distal end of the insertion tube will measure the size of the loop that is forming. If a large loop begins to form, the segment is stiffened and the distal tip is advanced further. When the distal tip reaches the left flexure, the segment that had been stiffened will be "loosened" (un-stiffened) to pass through the flexure. However, another segment, located in the sigmoid colon, will measure the loop formation, and the user will stiffen that segment to prevent a large loop from forming. It is noted that the user will straighten the insertion tube as required, and that the stiffening function is controlled by the user while the colonoscope is being straightened.

BRIEF DESCRIPTION OF THE FIGURES

FIG. 4 is a cross sectional view of a second flexible catheter segment of the medical instrument of FIG. 1 taken along lines 44 of FIG. 1 showing a second catheter stiffener, wherein the second flexible catheter segment is shown in a body lumen of a patient;

FIG. 5 is a cross sectional view of the second flexible catheter segment of FIG. 4 taken along lines 5-5 of FIG. 4 showing all four strain gages of the second loop sensor and with the body lumen and surrounding patient tissue and connections for the visualization and illumination devices omitted for clarity;

FIG. 6 is a view of the distal end of the medical catheter of FIG. 1 taken along lines 6-6 of FIG. 1 showing the visualization device and with proximal structure omitted for clarity;

DETAILED DESCRIPTION OF THE INVENTION

Figure 1:
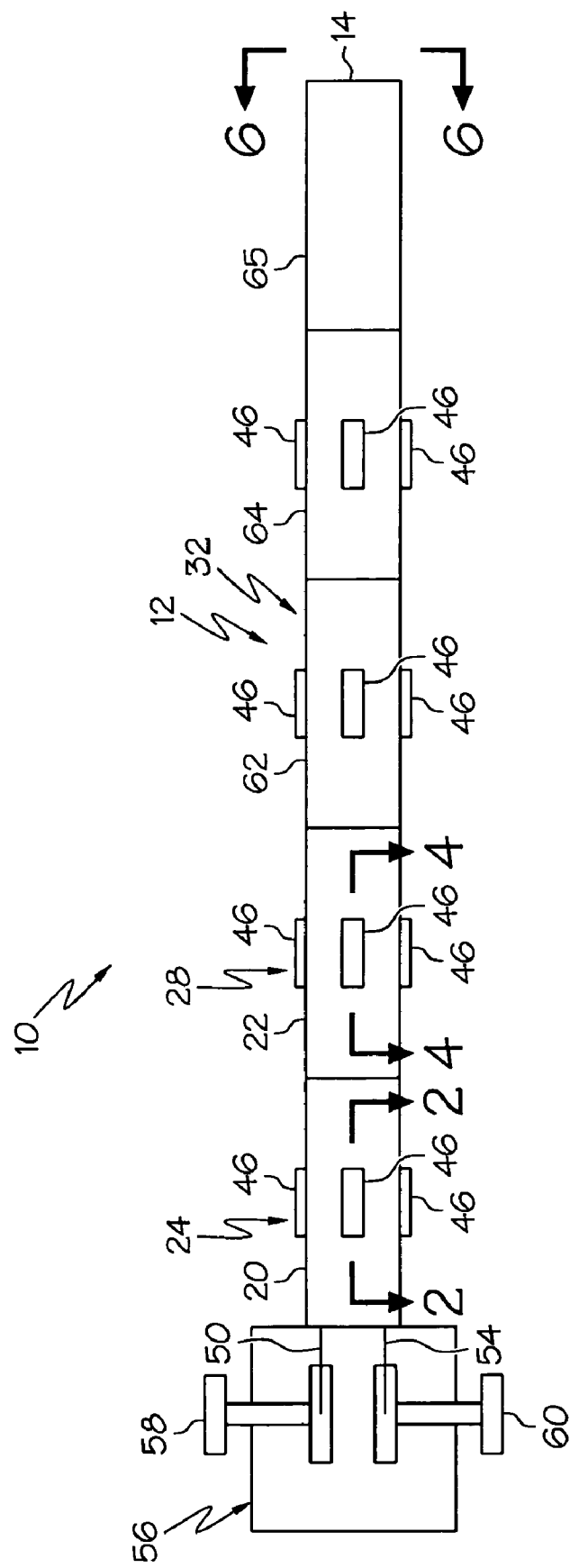
FIG. 1 is a schematic view of a first embodiment of a medical instrument including a medical catheter and a handpiece, wherein the handpiece is shown in cut-away.

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is understood that any one or more of the following-described expressions, embodiments, examples, etc. can be combined with any one or more of the other following-described expressions, embodiments, examples, etc.

Referring now to the Figures, wherein like numerals represent like elements throughout, FIGS. 1-8 illustrate a first embodiment of the invention. A first expression of the embodiment of FIGS. 1-8 is for a medical instrument 10 including a medical catheter 12. The medical catheter 12 has a distal end 14 (shown in FIG. 1) insertable within a body lumen 16 of a patient 18 (shown in FIG. 4), has a first flexible catheter segment 20, and has a second flexible catheter segment 22 disposed distal the first flexible catheter segment 20. The first flexible catheter segment 20 includes a first loop sensor 24 and includes an active first catheter stiffener 26 adapted to stiffen and un-stiffen substantially only the first flexible catheter segment 20. The second flexible catheter segment 22 includes a second loop sensor 28 and includes an active second catheter stiffener 30 adapted to stiffen and un-stiffen substantially only the second flexible catheter segment 22.

In one application of the first expression of the embodiment of FIGS. 1-8, the medical catheter 12 is a flexible endoscope insertion tube 32 having a visualization device 34 (shown in FIG. 6) disposed at the distal end 14. In one variation, the endoscope insertion tube 32 has an illumination device 36 disposed at the distal end 14. In one modification, the endoscope insertion tube 32 includes a working channel 38. In a different application, not shown in FIGS. 1-8, the medical catheter is a sheath adapted for installation over a flexible endoscope insertion tube. Non-endoscope applications are left to those skilled in the art.

Figure 7:
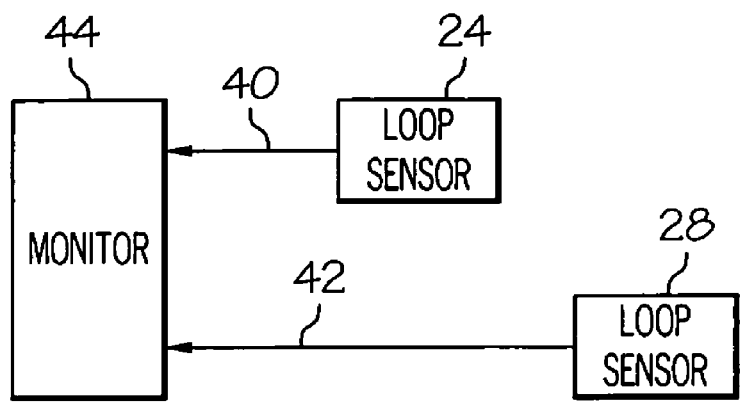
FIG. 7 is a schematic drawing showing the first output of the first loop sensor connected to a monitor and the second output of the second loop sensor connected to the monitor.

In one implementation of the first expression of the embodiment of FIGS. 1-8, as shown in FIG. 7, the first loop sensor 24 has a first output 40 and the second loop sensor 28 has a second output 42, wherein the first and second outputs 40 and 42 are available to a user of the medical instrument 10. In one variation, the first and second outputs 40 and 42 are displayed on a monitor 44. In the same or a different implementation, the first and second catheter stiffeners 26 and 30 are adapted to be independently activated by the user. In one example, the first and second catheter stiffeners 26 and 30 are adapted to be able to continuously vary the stiffness over a predetermined range. In another example, the first and second catheter stiffeners are adapted to be able to be switched either to a more flexible state or to a less flexible state.

Figure 8:
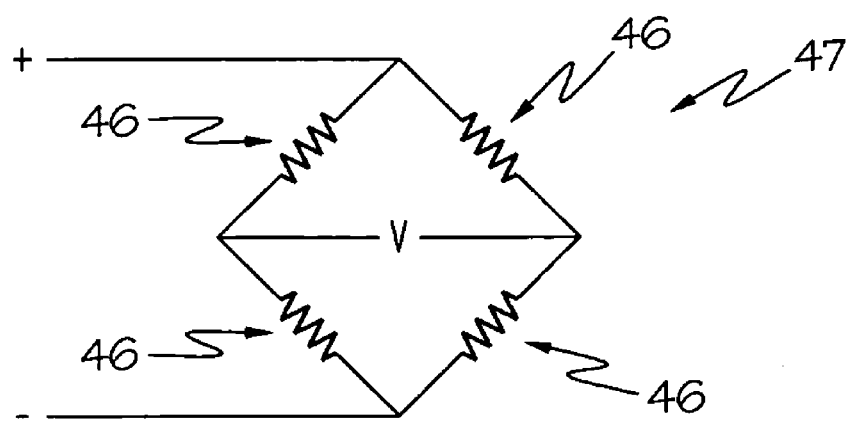
FIG. 8 is a schematic drawing showing the four strain gages of the first loop sensor configured as a Wheatstone bridge circuit, wherein "V" denotes the first output of the first loop sensor and wherein "+" and "−" denote an applied voltage.

In one enablement of the first expression of the embodiment of FIGS. 1-8, the first and second loop sensors 24 and 28 each include at least one strain gage 46. In one variation, the at least one strain gage 46 of the first loop sensor 24 includes four circumferentially arrayed strain gages 46 with circumferentially adjacent strain gages 46 of the first loop sensor 24 substantially equidistantly circumferentially spaced apart. In one modification, the four circumferentially arrayed strain gages 46 of the first loop sensor 24 are conventionally configured as a Wheatstone bridge circuit 47 (as shown in FIG. 8), wherein the first output 40 is a differential voltage output "V" of the Wheatstone bridge circuit 47. In one employment, the signal level of the differential voltage output "V" is proportional to the radius of the first flexible catheter segment 20, and the signal level of an undesirable loop is determined experimentally. In a different modification, each of the four circumferentially arrayed strain gages 46 of the first loop sensor 24 have a separate output available to the user. Depending on the number and arrangement of the strain gages 46 of the first loop sensor 24, the direction of looping can be determined (e.g., an output indicating compression of one strain gage and an output indicating extension of a circumferentially opposing strain gage). In one example, the at-least-one strain gage 46 of the second loop sensor 28 is substantially identical to the at-least-one strain gage 46 of the first loop sensor 24. Other types of loop sensors are left to those skilled in the art.

Figure 2:
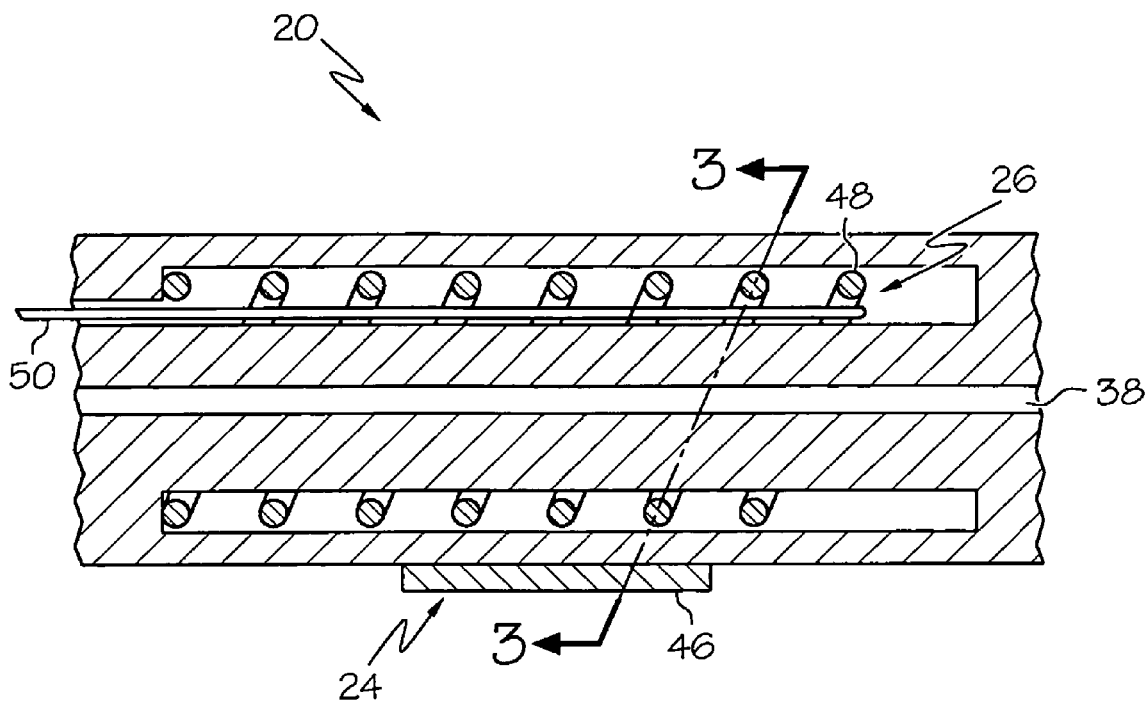
FIG. 2 is a cross sectional view of a first flexible catheter segment of the medical instrument of FIG. 1 taken along lines 2-2 of FIG. 1 showing a first catheter stiffener.
Figure 3:
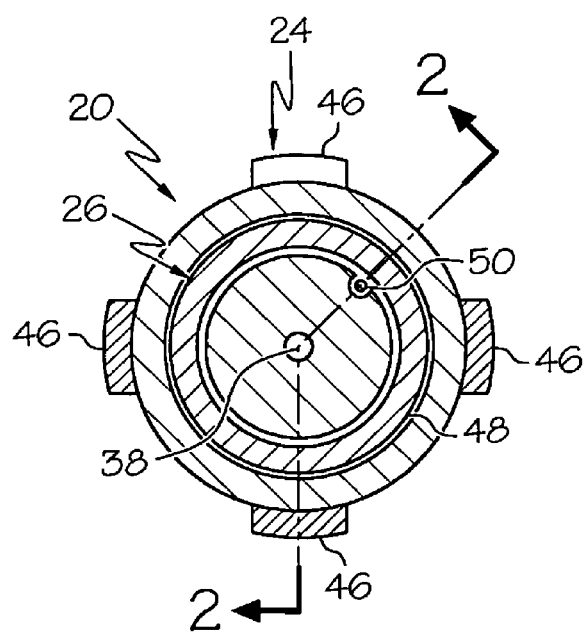
FIG. 3 is a cross sectional view of the first flexible catheter segment of FIG. 2 taken along lines 3-3 of FIG. 2 showing all four strain gages of the first loop sensor, wherein pull cables of distal flexible catheter segments and connections for the visualization and illumination devices have been omitted for clarity.

In a first employment of the first expression of the embodiment of FIGS. 1-8, the first catheter stiffener 26 includes a first helical coil 48 (also called a helical coil 48) surrounding a first pull cable 50 (also called a pull cable 50), as shown in FIGS. 2-3. In one variation, the first pull cable 50 is monolithically or otherwise attached to the distal end of the first helical coil 48, wherein the proximal end of the first helical coil 48 is blocked from proximal movement. By "monolithically attached" means the first pull cable and the first helical coil are two portions of one continuous piece. It is noted that when the user pulls on the first pull cable 50, the first helical coil 48 longitudinally compresses causing the first flexible catheter segment 20 to stiffen and when the user then releases the first pull cable 50, the first helical coil 48 longitudinally expands causing the first flexible catheter segment 20 to un-stiffen. In one employment, the first flexible catheter segment 20 tends to straighten when stiffened, and a stiffened first flexible catheter segment 20 resists further looping. In one modification, not shown, the first catheter stiffener includes at least one (and in one illustration three) additional helical coil surrounding a corresponding pull cable, wherein the helical coils are circumferentially arrayed with circumferentially adjacent helical coils substantially equidistantly circumferentially spaced apart. In one example, the second catheter stiffener 30 has a second helical coil 52 surrounding a second pull cable 54, as shown in FIGS. 4-5, and is substantially identical to the first catheter stiffener 26. In one arrangement, the medical instrument 10 also includes a handpiece 56 having first and second turn knobs 58 and 60, wherein the proximal end of the first pull cable 50 is operatively attached to the first turn knob 58 and the proximal end of the second pull cable 54 is operatively attached to the second turn knob 60.

In one extension of the first expression of the embodiment of FIGS. 1-8, the medical catheter 12 includes a third flexible catheter segment 62 and a fourth flexible catheter segment 64 each substantially identical to the first flexible catheter segment 20. In one variation, the medical catheter 12 includes a distal-most flexible catheter segment 65 which has an articulatable distal end portion and which is devoid of any loop sensor and/or catheter stiffener. In one variation, the distal-most catheter segment 65 has a length substantially identical to the length of the first flexible catheter segment 20.

In one configuration, not shown, each flexible catheter segment includes a plurality (such as four) circumferentially arrayed helical coils with corresponding pull cables and an equal plurality of likewise circumferentially arrayed strain gages. In one procedure, when a first strain gage indicates undesirable compression and a circumferentially-opposing second strain gage indicates undesirable expansion, the pull cable of the helical coil aligned with the second strain gage is pulled and the pull cable of the helical coil aligned with the first strain gage is relaxed, as can be appreciated by those skilled in the art.

Figure 9:
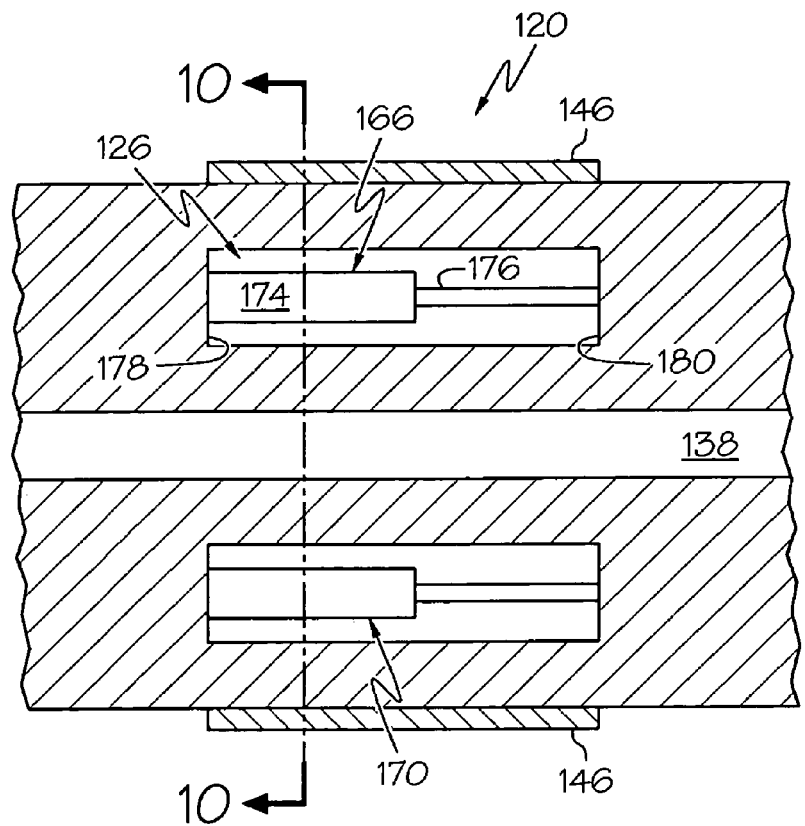
FIG. 9 is a view, as in FIG. 2, but of an alternate embodiment of the first flexible catheter segment of the first embodiment of FIG. 1 showing an alternate embodiment of a first catheter stiffener in the form of at least one solenoid (two of four solenoids are schematically shown in FIG. 9)
Figure 10:
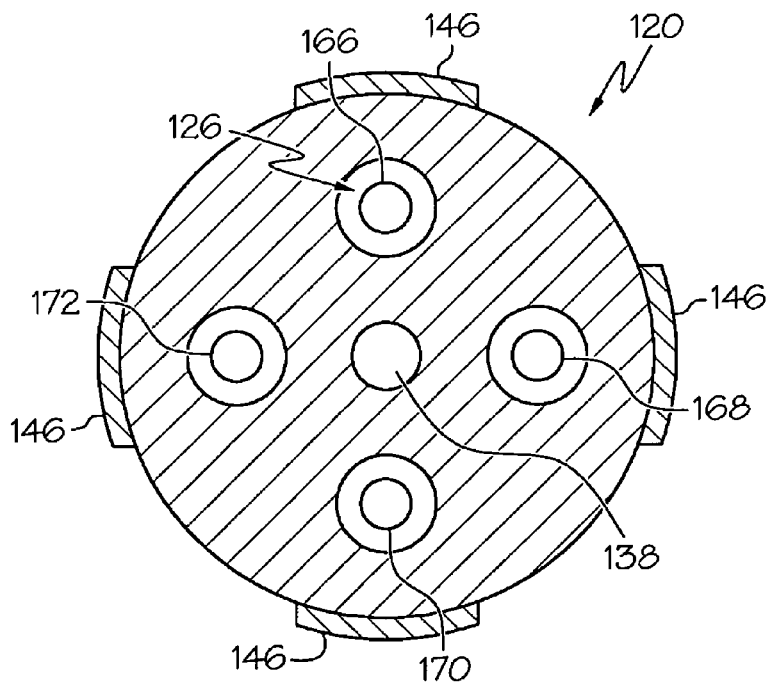
FIG. 10 is a view of the embodiment of FIG. 9 taken along lines 10-10 of FIG. 9 showing all four solenoids.

In a second employment, as shown in the alternative embodiment of the first flexible catheter segment 120 of FIGS. 9-10. the first catheter stiffener 126 includes at least one solenoid 166, 168, 170 and 172. Each solenoid, such as solenoid 166 has a stationary member 174 and a longitudinally movable member 176. In one configuration, the proximal end of the stationary member 174 is attached to an interior wall 178 of the first flexible catheter segment 120, and the distal end of the longitudinally movable member 176 is attached to an interior wall 180 of the first flexible catheter segment 120. When the solenoid 166 is activated, the longitudinally movable member 176 withdraws into the stationary member 174 pulling the interior walls 178 and 180 toward each other which longitudinally compresses and thus stiffens the first flexible catheter segment 120. When the solenoid 166 is de-activated, the longitudinally movable member 176 extends from the stationary member 174 relaxing the pulled-toward-each-other interior walls 178 and 180 which longitudinally expands and thus un-stiffens the first flexible catheter segment 120. In one employment, the first flexible catheter segment 120 tends to straighten when stiffened, and a stiffened first flexible catheter segment 120 resists further looping. In one variation, the at least one solenoid 166, 168, 170 and 172 includes four circumferentially arrayed solenoids 166, 168, 170 and 172 with circumferentially adjacent solenoids substantially equidistantly circumferentially spaced apart. Other types of catheter stiffeners are left to those skilled in the art. In one example, the first flexible catheter segment 120 includes strain gages 146 and a working channel 138.

In one configuration, each flexible catheter segment (such as the first flexible catheter segment 120 of FIG. 10, includes a plurality (such as four) circumferentially arrayed solenoids 166, 168, 170 and 172 and an equal plurality of likewise circumferentially arrayed strain gages 146. In one procedure, when a first strain gage (such as the top strain gage 146 in FIG. 10) indicates undesirable compression and the circumferentially-opposing strain gage (such as the bottom strain gage 146 in FIG. 10) indicates undesirable expansion, solenoid 170 is activated and solenoid 168 is not activated, as can be appreciated by those skilled in the art.

Figure 11:
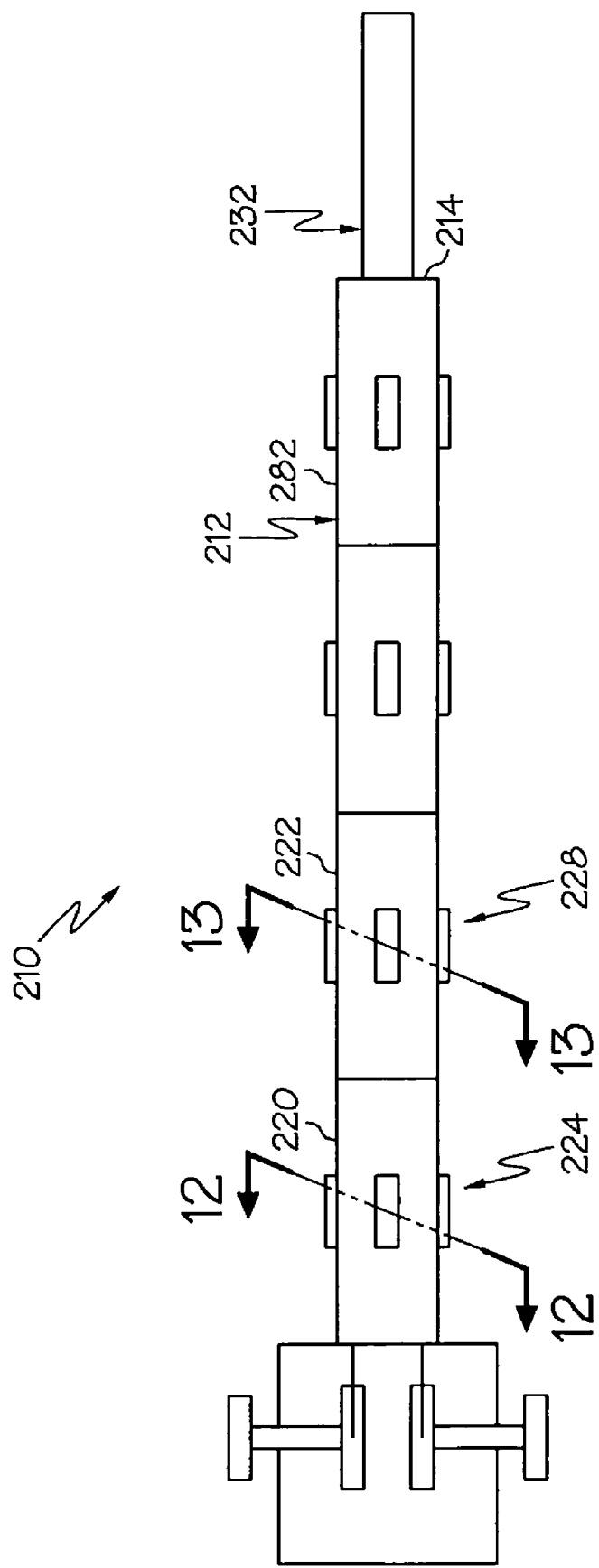
FIG. 11 is a view of a second embodiment of a medical instrument wherein the medical catheter is a sheath adapted for installation over a flexible endoscope insertion tube.
Figure 12:
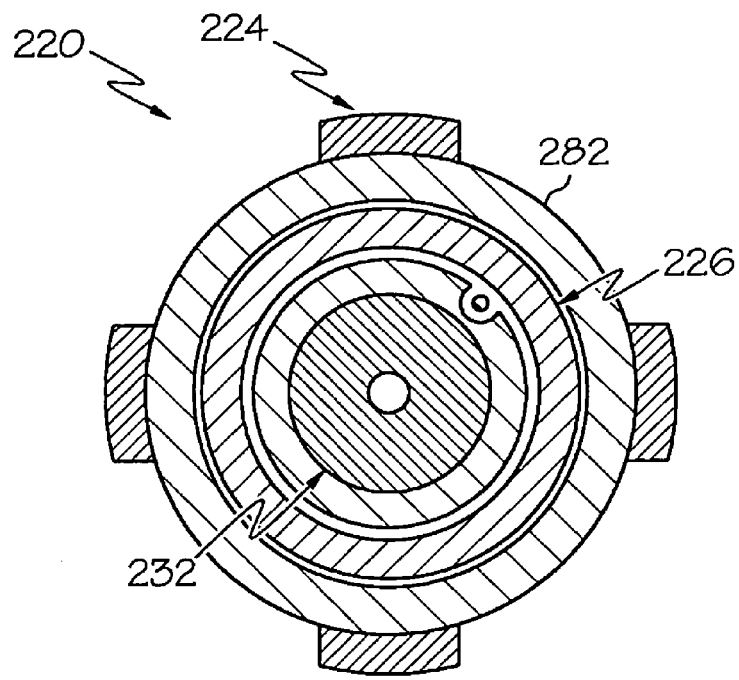
FIG. 12 is a view, as in FIG. 3, but of the second embodiment of FIG. 11.
Figure 13:
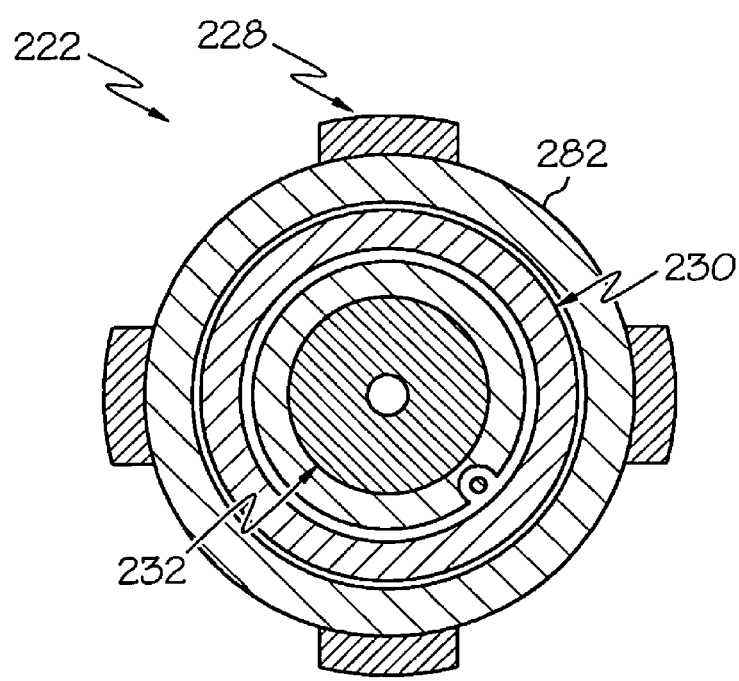
FIG. 13 is a view, as in FIG. 5, but of the second embodiment of FIG. 11.

A second embodiment of the medical instrument 210 of the invention is shown in FIGS. 11-13. A first expression of the embodiment of FIGS. 11-13 is for a medical instrument 210 including a medical catheter 212, wherein the medical catheter 212 is a sheath 282 and is adapted for installation (such as by sliding) over a flexible endoscope insertion tube 232 having a distal-tube-end visualization device (such as visualization device 34 of FIG. 6). The installed medical catheter 212 has a distal end 214 insertable within a body lumen of a patient (such as body lumen 16 of FIG. 4), has a first flexible catheter segment 220, and has a second flexible catheter segment 222 located distal the first flexible catheter segment 220. The first flexible catheter segment 220 includes a first loop sensor 224 and includes an active first catheter stiffener 226 adapted to stiffen and un-stiffen substantially only the first flexible catheter segment 220. The second flexible catheter segment 222 includes a second loop sensor 228 and includes an active second catheter stiffener 230 adapted to stiffen and un-stiffen substantially only the second flexible catheter segment 222.

It is noted that the variations, implementations, enablements, etc. of the embodiment of FIGS. 1-8, and the alternate embodiment of FIGS. 9-10 are equally applicable to the second embodiment of FIGS. 11-13.

A method of the invention is for using a medical instrument 10. The medical instrument 10 includes a medical catheter 12. The medical catheter 12 has a distal end 14 insertable within a body lumen 16 of a patient 18, has a first flexible catheter segment 20, and has a second flexible catheter segment 22 located distal the first flexible catheter segment 20. The first flexible catheter segment 20 includes a first loop sensor 24 and includes an active first catheter stiffener 26 adapted to stiffen and un-stiffen substantially only the first flexible catheter segment 20. The second flexible catheter segment 22 includes a second loop sensor 28 and includes an active second catheter stiffener 30 adapted to stiffen and un-stiffen substantially only the second flexible catheter segment 22. The method includes inserting the distal end 14 within the body lumen 16. The method also includes manually pushing the medical catheter 12 to advance the medical catheter 12 within the body lumen 16. The method also includes stopping manually pushing the medical catheter 12 upon determining from a visualization device 34 associated with the medical catheter 12 that the distal end 14 is no longer moving. The method also includes determining that undesirable looping is developing in the first flexible catheter segment 20 based at least on an output from the first loop sensor 24. The method also includes determining that undesirable looping is not developing in the second flexible catheter segment 22 based at least on an output from the second loop sensor 28. The method also includes using the first catheter stiffener 26 to stiffen the first flexible catheter segment 20. The method also includes not using the second catheter stiffener 30 to stiffen the second flexible catheter segment 22. The method also includes resuming manually pushing the medical catheter 12 after using the first catheter stiffener 26 to stiffen the first flexible catheter segment 20 and not using the second catheter stiffener 30 to stiffen the second flexible catheter segment 22.

In one utilization of the method, the body lumen is a colon of a human or other mammal. In another utilization, the body lumen is an upper gastrointestinal tract. In a further utilization, the body lumen is an artery lumen. Other body lumens are left to those skilled in the art.

Several benefits and advantages are obtained from one or more of the expressions of embodiments and the method of the invention. In a first example, having a multi-segment medical catheter with each segment having its own loop sensor and its own catheter stiffener to stiffen substantially only such segment allows a user more control in manually advancing the catheter within a body lumen of a patient. In one variation, a user stiffens only that segment or only those segments which are developing an undesirable loop as determined from the outputs of the loop sensors wherein such stiffening helps prevent further loop formation only in segments where needed while allowing flexibility in segments not developing an undesirable loop. In the same or a different variation, a user takes into account the location of the segments in the body lumen in deciding which segments should be stiffened.

In one utilization wherein the catheter is a flexible insertion tube of a colonoscope, when the distal tip of the insertion tube is being advanced through the sigmoid, the operator will articulate the distal end. In this example, when the distal tip is advanced into the descending colon, a segment just behind the distal end of the insertion tube will measure the size of the loop that is forming. If a large loop begins to form, the segment is stiffened and the distal tip is advanced further. When the distal tip reaches the left flexure, the segment that had been stiffened will be "loosened" (un-stiffened) to pass through the flexure. However, another segment, located in the sigmoid colon, will measure the loop formation, and the user will stiffen that segment to prevent a large loop from forming. It is noted that the user will straighten the insertion tube as required, and that the stiffening function is controlled by the user while the colonoscope is being straightened.

While the present invention has been illustrated by a description of several expressions of embodiments and a method, it is not the intention of the applicant to restrict or limit the spirit and scope of the appended claims to such detail. Numerous other variations, changes, and substitutions will occur to those skilled in the art without departing from the scope of the invention. For instance, the medical instrument of the invention has application in robotic assisted surgery taking into account the obvious modifications of such systems, devices and methods to be compatible with such a robotic system. It will be understood that the foregoing description is provided by way of example, and that other modifications may occur to those skilled in the art without departing from the scope and spirit of the appended Claims.

What is claimed is:

1. A medical instrument comprising a medical catheter having a distal end insertable within a body lumen of a patient, having a first flexible catheter segment, and having a second flexible catheter segment disposed distal the first flexible catheter segment, wherein the first flexible catheter segment includes a first loop sensor that provides a first output and includes an active first catheter stiffener adapted to stiffen and un-stiffen substantially only the first flexible catheter segment based on the first output, and wherein the second flexible catheter segment includes a second loop sensor that provides a second output and includes an active second catheter stiffener adapted to stiffen and un-stiffen substantially only the second flexible catheter segment based on the second output, wherein the first and second catheter stiffeners are adapted to be independently activated by the user, wherein the first catheter stiffener includes an expandedly-biased helical coil surrounding a pull cable, wherein the pull cable is attached to a distal end of the expandedly-biased helical coil to compress the expandedly-biased helical coil and stiffen the first flexible catheter segment, and wherein a proximal end of the expandedly-biased helical coil is blocked from proximal movement by the first flexible catheter section, wherein the distal end of the expandedly-biased helical coil is proximately translatable with respect to the first flexible catheter segment, and longitudinally compressible without corresponding compression of the first flexible catheter segment.

2. The medical instrument of claim 1, wherein the medical catheter is a flexible endoscope insertion tube having a visualization device disposed at the distal end.

3. The medical instrument of claim 1, wherein the first and second loop sensors each include at least one strain gage.

4. The medical instrument of claim 3, wherein the at least one strain gage of the first loop sensor includes four circumferentially arrayed strain gages with circumferentially adjacent strain gages of the first loop sensor substantially equidistantly circumferentially spaced apart.

5. The medical instrument of claim 4, wherein the four circumferentially arrayed strain gages of the first loop sensor are configured as a Wheatstone bridge circuit, wherein the first output is a differential voltage output of the Wheatstone bridge circuit.

6. The medical instrument of claim 4, wherein each of the four circumferentially arrayed strain gages of the first loop sensor provide a separate output, the separate outputs being displayed to the user for determination of the direction of looping by the user.

7. The medical instrument of claim 6, wherein the first catheter stiffener includes four correspondingly circumferentially arrayed stiffener mechanisms, the stiffener mechanisms each including an expandedly-biased helical coil surrounding a pull cable, wherein the pull cable is attached to a distal end of the helical coil to compress the helical coil and stiffen the first flexible catheter segment, and wherein the proximal end of the helical coil is blocked from proximal movement by the first flexible catheter section.

8. The medical instrument of claim 1, wherein the first catheter stiffener includes at least one additional expandedly-biased helical coil surrounding a corresponding pull cable, wherein the corresponding pull cable is attached to a distal end of the additional helical coil to compress the additional helical coil, wherein the proximal end of the additional helical coil is blocked from proximal movement by the first flexible catheter segment, and wherein the helical coils of the first catheter stiffener are circumferentially arrayed with circumferentially adjacent helical coils substantially equidistantly circumferentially spaced apart.

9. The medical instrument of claim 1, wherein the distal end of the medical catheter is an articulable distal end portion of a distal-most flexible catheter segment, and wherein the distal-most flexible catheter segment is devoid of any loop sensor and/or catheter stiffener.

10. A method for using a medical instrument, wherein the medical instrument includes a medical catheter having a distal end insertable within a body lumen of a patient, having a first flexible catheter segment, and having a second flexible catheter segment disposed distal the first flexible catheter segment, wherein the first flexible catheter segment includes a first loop sensor that provides a first output and includes an active first catheter stiffener adapted to stiffen and un-stiffen substantially only the first flexible catheter segment based on the first output, and wherein the second flexible catheter segment includes a second loop sensor that provides a second output and includes an active second catheter stiffener adapted to stiffen and un-stiffen substantially only the second flexible catheter segment based on the second output, wherein the first and second catheter stiffeners are adapted to be independently activated by the user, wherein the first catheter stiffener includes an expandedly-biased helical coil surrounding a pull cable, wherein the pull cable is attached to a distal end of the expandedly-biased helical coil to compress the expandedly-biased helical coil and stiffen the first flexible catheter segment, and wherein a proximal end of the expandedly-biased helical coil is blocked from proximal movement by the first flexible catheter section, wherein the distal end of the expandedly-biased helical coil is proximately translatable with respect to the first flexible catheter segment, and longitudinally compressible without corresponding compression of the first flexible catheter segment, and wherein the method comprises:
  a) inserting the distal end within the body lumen;
  b) manually pushing the medical catheter to advance the medical catheter within the body lumen;
  c) stopping manually pushing the medical catheter upon determining from a visualization device associated with the medical catheter that the distal end is no longer moving;
  d) determining that undesirable looping is developing in the first flexible catheter segment based at least on an output from the first loop sensor;
  e) determining that undesirable looping is not developing in the second flexible catheter segment based at least on an output from the second loop sensor;
  f) using the first catheter stiffener to stiffen the first flexible catheter segment;
  g) not using the second catheter stiffener to stiffen the second flexible catheter segment; and
  h) resuming manually pushing the medical catheter after using the first catheter stiffener to stiffen the first flexible catheter segment and not using the second catheter stiffener to stiffen the second flexible catheter segment.

11. A medical catheter comprising:
  a distal end insertable within a body lumen of a patient; a first flexible catheter segment including a first loop sensor that provides a first output and an active first catheter stiffener adapted to stiffen and un-stiffen substantially only the first flexible catheter segment based on the first output, wherein the first catheter stiffener includes a first expandedly-biased helical coil having a first pull cable connected thereto, wherein the pull cable is attached to a distal end of the first expandedly-biased helical coil to compress the first expandedly-biased helical coil and stiffen the first flexible catheter segment, and wherein a proximal end of the first expandedly-biased helical coil is blocked from proximal movement by the first flexible catheter section; and
  a second flexible catheter segment disposed distal the first flexible catheter segment, wherein the second flexible catheter segment includes a second loop sensor that provides a second output and includes an active second catheter stiffener adapted to stiffen and un-stiffen substantially only the second flexible catheter segment based on the second output, wherein the second catheter stiffener includes a second expandedly-biased helical coil having a second pull cable connected thereto, wherein the pull cable is attached to a distal end of the helical coil second expandedly-biased to compress the second expandedly-biased helical coil and stiffen the second flexible catheter segment, and wherein a proximal end of the second expandedly-biased helical coil is blocked from proximal movement by the second flexible catheter section, wherein the distal end of the first expandedly-biased helical coil is proximately translatable with respect to the first flexible catheter segment, and longitudinally compressible without corresponding compression of the first flexible catheter segment, and wherein the distal end of the second expandedly-biased helical coil is proximately translatable with respect to the second flexible catheter segment, and longitudinally compressible without corresponding compression of the second flexible catheter segment.

12. The medical instrument of claim 11, wherein the distal end of the medical catheter is an articulable distal end portion of a distal-most flexible catheter segment, and where in the distal-most flexible catheter segment is devoid of any loop sensor and/or catheter stiffener.

13. The medical instrument of claim 11, wherein the first catheter stiffener includes at least one additional expandedly-biased helical coil surrounding a corresponding pull cable, wherein the corresponding pull cable is attached to a distal end of the additional expandedly-biased helical coil to compress the additional expandedly-biased helical coil, wherein the proximal end of the additional expandedly-biased helical coil is blocked from proximal movement by the first flexible catheter segment, and wherein the first expandedly-biased helical coil of the first catheter stiffener is circumferentially arrayed with circumferentially adjacent helical coils substantially equidistantly circumferentially spaced apart.

* * * * *